United States Patent [19]
Chio et al.

[11] Patent Number: 5,879,307
[45] Date of Patent: Mar. 9, 1999

[54] NON-INVASIVE METHOD AND APPARATUS FOR DIAGNOSING AND MONITORING AORTIC VALVE ABNORMALITIES, SUCH A AORTIC REGURGITATION

[75] Inventors: Shiu-Shin Chio, San Diego, Calif.; Todd Brinton, North Chicago, Ill.

[73] Assignee: Pulse Metric, Inc., San Diego, Calif.

[21] Appl. No.: 816,988

[22] Filed: Mar. 13, 1997

Related U.S. Application Data

[60] Provisional application No. 60/015,719 Mar. 15, 1996.
[51] Int. Cl.$^6$ .................................................. A61B 05/00
[52] U.S. Cl. ........................................ 600/485; 600/500
[58] Field of Search .................................. 600/485, 490, 600/493–7, 500–3

[56] References Cited

U.S. PATENT DOCUMENTS

| | | | |
|---|---|---|---|
| 4,664,125 | 5/1987 | Ointo | 600/485 |
| 4,880,013 | 11/1989 | Chio . | |
| 5,000,188 | 3/1991 | Kojima | 600/500 |
| 5,162,991 | 11/1992 | Chio . | |
| 5,582,179 | 12/1996 | Shimizu et al. | 600/500 |
| 5,634,467 | 6/1997 | Nevo | 600/493 |
| 5,730,137 | 3/1998 | Amano et al. | 600/500 |

OTHER PUBLICATIONS

Shiota, Takahiro, M.D et al.; *Effective Regurgitant Orifice Area by the Color Doppler Flow Convergence Method for Evaluating the Severity of Chronic Aortic Regurgitation*; Feb. 1, 1996; Circulation, vol. 93, No. 3, pp. 594–602.

Ishii, Masahiro, M.D. et al.; *Evaluation of eccentric aortic regurgitation by color Doppler jet and color Doppler–imaged vena contracta measurements: An animal study of quantified aortic regurgitation*; Oct., 1996; American Heart Journal; pp. 796–804.

Tamai, Takuya, M.D. et al; *Evaluation of Aortic Regurgitation Using Cine Magnetic Resonance Imaging*; Nov., 1993; Jpn. Heart J.; pp. 741–748.

*Primary Examiner*—Robert L. Nasser
*Attorney, Agent, or Firm*—Bose McKinney & Evans

[57] ABSTRACT

A method and device is provided for determining aortic valve abnormalities. The method first includes the step of providing a sphygmomanometer device for inducing a pressure on a body part of a patient. A data stream receiver is provided for receiving a stream of data relating to the pressure response of the pulsed fluid flowing through the cardiovascular system of the patient. A data processor is provided for processing the data to create a series of time dependant pulse wave forms. The data can be converted by Fast Fourier Transformation (FFT) to obtain Power Spectrum (PS) which comprises a frequency dependant array of pulse signals. Both of the time dependant and frequency dependant (Power Spectrum) data can be displayed and analyzed to help determine the condition of the aortic valve and the percentage of regurgitation of the patient. With the Power Spectrum display, the determination is made based on first, identifying the existence of an additional second series of harmonically occurring regurgitation signals that have a frequency different from the main signals indicative of the forward flow of fluid through the aortic valve. The ratio of the amplitude or density of the regurgitation signal peak can be divided by the amplitude or density of the associated main signal peak, to determine the ratio of the associated "Regurgitation" flow to and "Main" flow, to thereby semi-quantitatively determine the percent of regurgitation flow of the patient.

32 Claims, 10 Drawing Sheets

NON-INVASIVE METHOD AND APPARATUS FOR DIAGNOSING AND MONITORING AORTIC VALVE ABNORMALITIES, SUCH A AORTIC REGURGITATION

This patent application is a continuation-in-part of provisional patent application No. 60/015,719, filed on 15 Mar. 1996.

I. TECHNICAL FIELD OF THE INVENTION

The present invention relates to a method and apparatus for determining the cardiovascular condition of a patient, and more particularly to a method and apparatus for monitoring aortic valve abnormalities such as aortic regurgitation.

II. BACKGROUND OF THE INVENTION

A. The Pathology of Aortic Regurgitation.

Heart valve abnormalities are a major component of cardiovascular disease. Aortic Regurgitation (AR), also known as Aortic Insufficiency (AI), is probably the most common valvular problem. Each year thousands of patients experience cardiovascular function problems as a result of aortic regurgitation. Eventually many of these cases lead to the need for surgical intervention such as aortic valve replacement. Therefore, the detection and evaluation of aortic regurgitation is extremely important in those subjects with suspected cardiovascular disease. The development of a simple, inexpensive technique by which to screen individuals for aortic regurgitation is extremely important in those subjects with suspected cardiovascular disease. The development of a simple, inexpensive technique and apparatus with which one can screen individuals for aortic regurgitation represents an advance in medical instrumentation.

Aortic regurgitation may be caused by a variety of diseases or acute trauma. In the case of disease, the process may act directly on the aortic valve leaflet or the wall of the aortic root. Approximately two-thirds of severe aortic regurgitation cases which result in aortic valve replacement are caused by leaflet abnormalities. As used in this application, the term "aortic valve abnormalities" is broad enough to encompass all of the various conditions which result in aortic regurgitation.

Rheumatic fever is a common disease mechanism of many valve leaflet abnormalities. The fever causes the cusps to become infiltrated with fibrous tissues and retract, a process that prevents the cusps from closing during diastole. This usually results in AR in the left ventricle through the center of the valve. Diseases such as infective endocarditis may cause aortic regurgitation through a similar mechanism.

In contrast, diseases such as Syphilis, Ankylosing Spondylitis, Rheumatoid Arthritis, and Marfan Syndrome may produce aortic regurgitation by causing marked dilation of the ascending aorta. In each of these diseases, the aortic annulus may become greatly dilated, the aortic leaflets may separate, and AR may ensue. In addition, the dilation of the aortic root may have a secondary effect on the aortic valve, since it may cause tension and bowing of the cusps which may thicken, retract, and become too short to close the aortic orifice.

Acute trauma may produce aortic regurgitation as a result of mechanical damage. For example, a tear in the ascending aorta may cause loss of valve leaflet support and therefore lead to the initiation of regurgitation.

Regardless of the etiology, Aortic Regurgitation usually produces dilation and hypertrophy of the left ventricle as a result of the chronic regurgitant flow. It may also produce dilation of the mitral valve ring and the left atrium. These changes represent cardiovascular system adaptation as a result of chronic or gradually increasing aortic regurgitation. The systemic response permits the ventricle to perform as an effective high compliance pump. As a result, patients with severe chronic AR have the largest end-diastolic volumes of those with any form of heart disease.

High end-diastolic and stroke volumes assist in maintaining proper cardiovascular function. As the left ventricle dilates, ventricular function deteriorates due to the inability to efficiently move blood out of the heart. Rising end-diastolic volumes eventually cannot compensate for the regurgitant volume, and the ejection fraction and forward stoke volume decline. In order to restore forward stroke volume and ventricular function, aortic valve replacement usually must be performed.

Unfortunately, the cardiovascular system cannot adapt quickly to acute aortic regurgitation. As a result, the back flow of blood through the damaged valve will fill the ventricle. A ventricle of normal size cannot accommodate the combined large regurgitate volume and atrium inflow. Since total stroke volume cannot rise due to structural constraints, forward stroke volume will decline. In response, left ventricle diastolic pressure may rise quickly, and cardiac function may drop drastically. Cardiovascular complications may ensue quickly threatening the life of the patient.

B. Prior Art Methods for Detecting and Evaluating Aortic Regurgitation.

The state-of-the-art methods for detecting aortic regurgitation and either evaluating the severity of disease or quantifying the amount of regurgitate volume include echocardiography, invasive catheterization, and magnetic resonance imaging (MRI).

A variety of echocardiography techniques can be utilized to evaluate aortic regurgitation. Although M-mode or two-dimensional ultrasound may be quite useful to detect aortic regurgitation or structural changes, the addition of Doppler may be quite useful to measure the outflow velocity from the aortic valve. When combined with measurements of valve diameter, the flow can be calculated. Color flow Doppler represents a drastic improvement in echo imaging due to the ability to approximate the regurgitate volume. Additionally, continuous wave Doppler may also be a useful technique to evaluate the severity of the disease in which the deceleration slope of the ventricular pressure gradient is evaluated. This is accomplished using the Bernoulli equation which relates velocity changes to a pressure gradient.

Invasive techniques may also be used to evaluate aortic regurgitation. Many of these invasive techniques utilize a scale from 1 to 4+ to evaluate the severity of the aortic regurgitation. This is accomplished using angiography techniques to review the degree of regurgitate back flow through the aortic valve.

Recently, however, major advances have been made using MRI to evaluate aortic regurgitation. MRI can be used to simultaneously evaluate the severity of both aortic regurgitation and left ventricle dysfunction. Past MRI techniques utilized multiple tomographic planes which made the process time consuming and difficult to analyze. In addition, the techniques focused simply on the size of the regurgitate flow jet, which has a poor correlation to regurgitate volume. However, recently developed techniques utilize a rapid single-plane cine MRI technique which can be completed in less than 10 minutes. The new technique incorporates a new grading system which is based on the presence, size, and persistence of not only the regurgitate jet, but also the zone of proximal signal loss.

Unfortunately, invasive catheter procedures, echocardiography, and MRI are associated with several problems which may limit routine clinical utilization. Invasive catheterization, for example, is extremely expensive due to the cost of the physician, support personnel, and hospital overhead. These procedures may also be associated with considerable patient risk due to their invasive nature. Additionally, although highly accurate, these procedures are quite time-consuming to perform and usually require an overnight hospital stay. Therefore, few individuals undergo evaluation of aortic regurgitation using invasive techniques.

Non-invasive echocardiography procedures may reduce costs since they can be performed on an out-patient basis, however, they still require the cost of highly skilled personnel. Echocardiography is usually performed by a highly skilled technician and study results are usually evaluated by a specialized physician (cardiologist). Reproducibility may be of concern, however, since results may vary depending on the placement of the non-invasive transducer and the ability of the operator. In addition, the use of two-dimensional imaging may potentially underestimate or overestimate the size of physiological structures since the third dimension in space cannot be evaluated. Potential patient risk may be minimized due to the non-invasive nature of the procedure. However, the time requirements may still potentially limit utilization in some patients.

Although the development of new MRI techniques may represent an advance in the clinical assessment of aortic regurgitation, the expense of such procedures is of great concern. MRI equipment is extremely expensive, and patient access is quite limited. Importantly, although no biological after-effects have been seen from MRI, the body is exposed to low energy radiation which could be potentially hazardous. Further, the operation of an MRI requires highly skilled operators including qualified technicians and a specialized physician (radiologist). Although new methods may reduce procedure time, patient preparation time is still considered very significant.

Room for improvement exists over the known methods for determining aortic regurgitation. In particular, improvement can be achieved by providing a reliable method for determining the existence of aortic regurgitation, and a method for enabling the physician to perform a semi-quantitative analysis of the volume of aortic regurgitation, which does not require an invasive procedure. Further, the state of the known art would be improved by the existence of a method for determining and quantifying aortic regurgitation that can be performed easily by relatively low cost personnel, especially if the method could be performed on the patient without the need for expensive equipment.

It is therefore one object of the present invention to provide a method and apparatus for determining the existence of aortic valve abnormalities of the type that cause aortic regurgitation. It is also an object of the present invention to provide a method and apparatus that can enable a practitioner to determine the existence of aortic regurgitation, and to perform a semi-quantitative analysis of the relative volume of aortic regurgitation.

It is a further object of the present invention to provide a method and apparatus for determining aortic regurgitation which does not require expensive equipment or invasive procedures.

III. SUMMARY OF THE INVENTION

In accordance with the present invention, a method is provided for identifying the existence of aortic valve abnormalities in a patient. The method comprises the steps of providing a pressure inducing means for inducing a pressure to a body part of a patient. A data receiving means is provided, which is used for receiving a stream of pulsation signal data from the patient relating to pressure response of pulsed fluid flowing through the cardiovascular system of the patient. A data processing means processes the stream of data to create an array of pulse wave forms. Wave form characteristics are then identified that denote the presence of aortic valve abnormalities.

Preferably, the data processing means is used to create a time dependant array of pulse wave forms which is graphically displayed by a graphic display means, such as a computer monitor or a paper printout.

Also, each of the pulse wave forms of the time dependant array of pulse wave forms can include a peak. Wave form characteristics that indicate the presence of aortic valve abnormalities can be identified by comparing the heights of a series of adjacent wave form peaks. The graphic display of the time dependant array can include an envelope line that extends between the peaks of adjacent wave forms. The slope of the envelope line can be used to identify the existence of aortic valve abnormalities. If the envelope line has an undulating slope, the presence of aortic valve abnormalities is suggested.

In an alternate embodiment, the time dependent wave form data can be converted to frequency dependant wave form data through the use of a Fourier transformation. Characteristics of the frequency dependant wave form data can be identified which suggest the presence of aortic regurgitation. These characteristics are identified by first identifying a first series of harmonically occurring flow signals that correspond to a "main" flow of fluid forwardly through the aortic valve, and then detecting the presence or absence of a second series of harmonically occurring "regurgitation" flow signals corresponding to the aortic regurgitation. The first and second series of signals each have an amplitude. By comparing the amplitude $A_2$ of a flow signal of the second series to the amplitude $A_1$ of a flow signal of the first series, a semi-quantitative analysis of the aortic regurgitation can be performed. Additionally, a semi-quantitative relative value for the aortic regurgitation can be obtained by comparing the density $D_2$ of the flow signal of the second series to the density $D_1$ of the flow signal of the first series.

In accordance with another aspect of the present invention, a device is provided for identifying the existence of aortic valve abnormalities in a patient which comprises a pressure inducing means for inducing a pressure to a body part of a patient, a data receiving means for receiving a stream of pulsation signal data from the patient relating to the pressure response of pulsed fluid flowing through the cardiovascular system of the patient. A data processing means is provided for processing the stream of data to create a time dependant array of pulse wave forms. Means are provided for aiding in the identification of wave form characteristics that denote the presence of aortic valve abnormalities.

One feature of the present invention is that it enables the user to identify characteristics that denote the presence of aortic valve abnormalities (and hence, aortic regurgitation) through the use of a non-invasive pressure inducing means. This feature has the advantage of enabling the physician to determine and diagnose a condition through the use of a procedure which is minimally invasive, and which can be performed at low cost. This feature has the further advantage of enabling testing to be conducted for aortic valve abnormalities for a wide number of people, thus making such a test affordable enough to be employed as a "screening" test.

Another feature of the present invention is that data is provided which includes a first series of signals indicative of the flow of fluid forwardly through the aortic valve, and a second series of signals indicative of aortic valve regurgitation. By comparing these two signals, a semi-quantitative analysis of the volume of aortic regurgitation can be obtained. This feature has the advantage of enabling the user to obtain some quantitative data about the extent of aortic regurgitation, which is indicative of the severity of the patient's problems.

Another advantage of this invention is that the procedure can be performed during routine blood pressure measurement. As a result, the procedure should take no more than a few minutes or so, with an automated computer having fast Fourier transformation (FFT) and Power Spectrum Display (PSD) programs. Due to the use of a non-invasive cuff sphygmomanometer, the procedure should be useable by personnel having no special training for operation. Importantly, patient risk from the procedure is almost non-existent, being no greater than the risk associated with routine blood pressure measurement.

Another advantage is that personnel training time is minimized as similar devices, using oscillometric technology, are used routinely every day in hospitals and physician offices around the world. Additionally, the cost of performing the procedure should be low compared to the other state-of-the-art technologies discussed previously. Also, the use of computer automation and analysis techniques should enable the user to achieve accurate evaluations of aortic valve irregularities.

These and other features and advantages of the present invention will become apparent to those skilled in art upon a review of the detailed description of the preferred embodiment of the present invention, which presently represents the best mode perceived by the inventors of practicing this invention.

IV. BRIEF DESCRIPTION OF THE DRAWINGS

V. DETAILED DESCRIPTION

Figure 7:
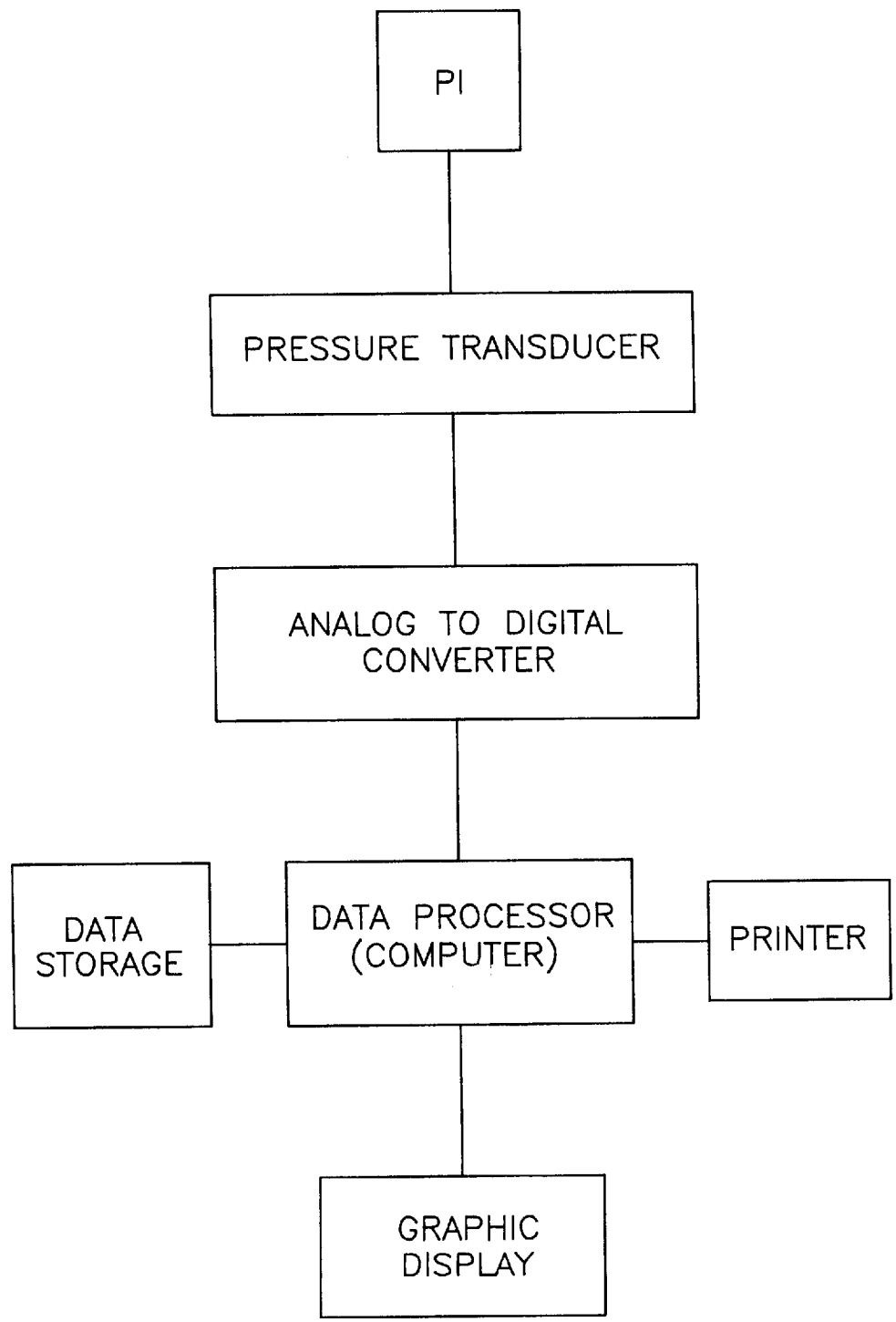
FIG. 7 represents a diagrammatic representation of the components of the present invention.

This invention uses the same apparatus and data obtaining means as is disclosed in Chio U.S. Pat. Nos. 4,880,013 and 5,162,991, the disclosure of which is incorporated herein by reference. The products discussed in the Chio patents are commercially available as the Dynapulse® blood pressure monitor from Pulse Metric® Inc. of San Diego, Calif. 92121. To briefly restate that which is disclosed in the earlier Chio references, your attention is now directed to FIG. 7.

The apparatus of the present invention includes a non-invasive pressure inducing means such as a cuff 10 for exerting a pressure on a body part, such as an arm. Although a wide variety of pressure inducing means can be used, the pressure inducing means preferably comprises an inflatable cuff 10 which can be wrapped around the limb of a patient. Typically, such an inflatable cuff 10 includes a pump means (either manually actuated or electronically actuated) which pumps air into the interior of the cuff to exert pressure on the body part. An example of such a cuff 10 is the cuff supplied with the DYNAPULSE blood pressure monitor manufactured by Pulse Metric, Inc. of San Diego, Calif., the assignee of the present invention. Most other available blood pressure cuffs work in a similar manner.

A transducer means 16 is provided for picking up the total pressure induced signals, including the background pressure signals and the small oscillation (pulsation) signals. The transducer means 16 converts these pressure signals that are picked up into electrical signals. Typically, the background pressure signals are picked up as DC signals, and the pulsation signals are picked up as AC signals. These signals are picked up over a period of time, and thus, give rise to a time dependant array of pulsation signals.

The pressure transducer 16 primarily comprises a solid state pressure sensor or similar device that is capable of picking up pressure signals and converting these pressure signals into an analog electrical signal for transmission from the transducer means 16. An example of a pressure transducer that will work well with the present invention is the pressure transducer found within the DYNAPULSE device described above. Preferably, the pressure transducer 16 has a linear response rate, or has a known correlation between the input pressure received by the transducer 16 and the output electrical signal (e.g. voltage sent out by the transducer.) The transducer 16 generates a voltage signal which comprises a generally continuous overall pressure data stream 20. The overall pressure data stream 20 is sent in a generally continuous manner, over time, to the analog-to-digital converter 26. The analog-to-digital converter 26 converts the analog information provided by the transducer 16 into digital information.

A digitized pressure data stream 30 is fed from the analog-to-digital converter 26 to a data processing means such as a computer 36. As with data stream 20, the digitized data stream 30 represents an essentially continuous stream of data taken over a period of time. The computer data processing means should preferably be an IBM compatible computer. The speed and capabilities of the computer necessary to perform the tasks of the present invention are dictated largely by the complexity of the software. However, all the tasks described above can be accomplished with a computer as limited in capabilities as a 1988 or 1989 vintage IBM XT or AT computer using an 8086 or 80286 Intel processing chip, and of course can be accomplished with any of the more recent, more powerful IBM compatibles (e.g. 80586 or 80680) devices.

As will be appreciated, the heart of the data processing means (computer 36) is the software that directs the computer on how to process the data that is fed into it through the digitized data stream 30. The exact nature of the software will be described in more detail below.

The computer 36, through its software, processes the data to translate the data into a usable information stream. This useful information stream can be for example (1) a stream 40 that is forwarded to a graphic display, such as a computer monitor 42; (2) a printer-readable information stream 44 that is fed to a printer 46; and/or (3) a stream 48 fed to a data storage means, such as a hard drive 50, a floppy disc, or compact disc.

An appropriate pressure transducer 16 and analog-to-digital converter 26 are provided with the DYNAPULSE blood pressure monitoring system, which also includes a pressure inducing cuff 10. The data storage device 50, monitor 42, printer 46 and computer 36 are of the type that are available from any one of several computer manufacturers (such as Gateway and Compaq); printer manufacturers (e.g. Hewlett Packard, and Canon); and monitor manufacturers (e.g. Samsung, and NEC).

The first step in the process of the present invention is to gather data from the patient of interest. The manner in which the data is gathered from the patient is similar to the manner discussed in the above referenced Chio '013 and '991 patents. The cuff 10 is affixed to the patient and operated in accordance with its usual operating procedures. Pressure is induced by the pressure inducing means on the patient's body part which is above the normal systolic blood pressure of the patient. This supra systolic blood pressure that is induced on a patient is typically between 140 and 250 mmHg, depending upon the normal systolic blood pressure of the patient. Over a period of time, typically lasting between about 20 and 60 seconds, the pressure that is induced by the pressure inducing means is gradually reduced, in a manner very much identical to the manner in which the induced pressure is reduced during a blood pressure measurement. Preferably, the cuff pressure is decreased in a smooth manner during the test period, a smooth decrease in pressure facilitates the construction and interpretation of the graphic displays produced by the instant invention.

When the test begins, the pressure induced by the pressure inducing means 10 is at a supra systolic pressure. As the test progresses, the pressure continues to decrease past the point wherein the pressure induced by the pressure inducing means 10 equals the patient's systolic pressure. The pressure induced by the pressure inducing means 10 continues to decrease past the point of the patient's mean arterial pressure (MAP), and past the point where the pressure induced by the pressure inducing means 10 equals the patient's diastolic pressure. The pressure then continues to decrease, so that data is obtained at a subdiastolic pressure, which is a pressure that is below the patient's measured diastolic pressure. It has been found by the applicant that the best results are achieved from data obtained at either supra systolic pressure, or subdiastolic pressures.

The pressure transducer 16 comprises a data receiving means for receiving a stream of pulsation signal data from the patient that relates to the pressure response of a pulsed fluid, such as blood, that is flowing through the cardiovascular system of the patient. This pulsation signal data is then processed by the analog-to-digital converter 26 and the computer 36, both of which perform some data processing functions.

The primary data processor (the computer 36) is asked to perform three primary functions within the present invention. As such, three different items of software are required to perform these functions, although it will be appreciated, that all three software components can be packaged together within a single software "package".

The first function performed by the data processor is to collect the data that is being fed to it through the overall pressure data stream 30, and to perform the necessary processing of the data so that it provides useful information, when in its time dependant display mode. This program is the "Dynapulse®" program that is available from Pulse Metric, Inc. of San Diego, Calif., U.S.A. A second software function performed by the computer and its software is to convert the time dependant array of pulse wave forms into an array of frequency dependant wave forms. This is accomplished through a Fourier transformation program. Fourier transformation programs are available, and the fast Fourier transformation (FFT) and Power Spectrum Display (PSD) programs that will function well with the present invention can be obtained from, William H. Press et al., *Numerical Recipes in C,* 2nd ed., Cambridge University Press, 1992. For displaying the various information in a graphic display, the applicants have found that the Excel® program sold by the Microsoft® Corporation of Seattle, Wash., U.S.A. performs adequately for the tasks demanded by the present invention.

Figure 1A:
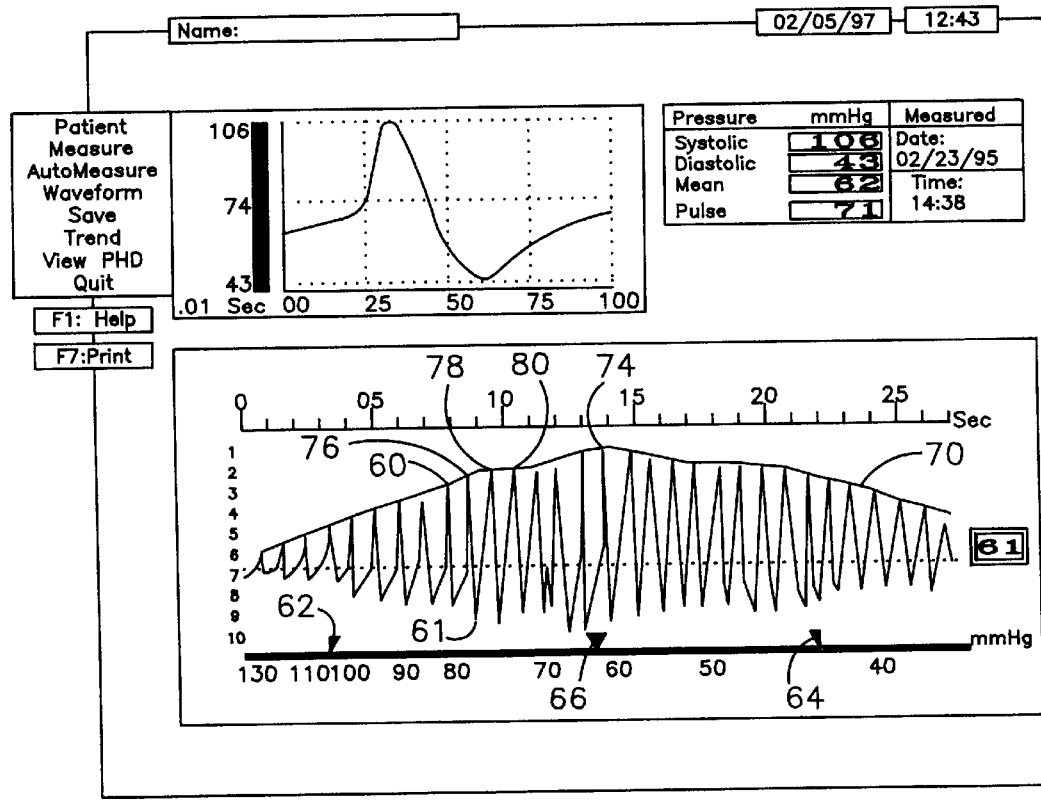
FIGS. 1a and 1b represent displays of pulsation signal data taken from two normal patients.
Figure 1B:
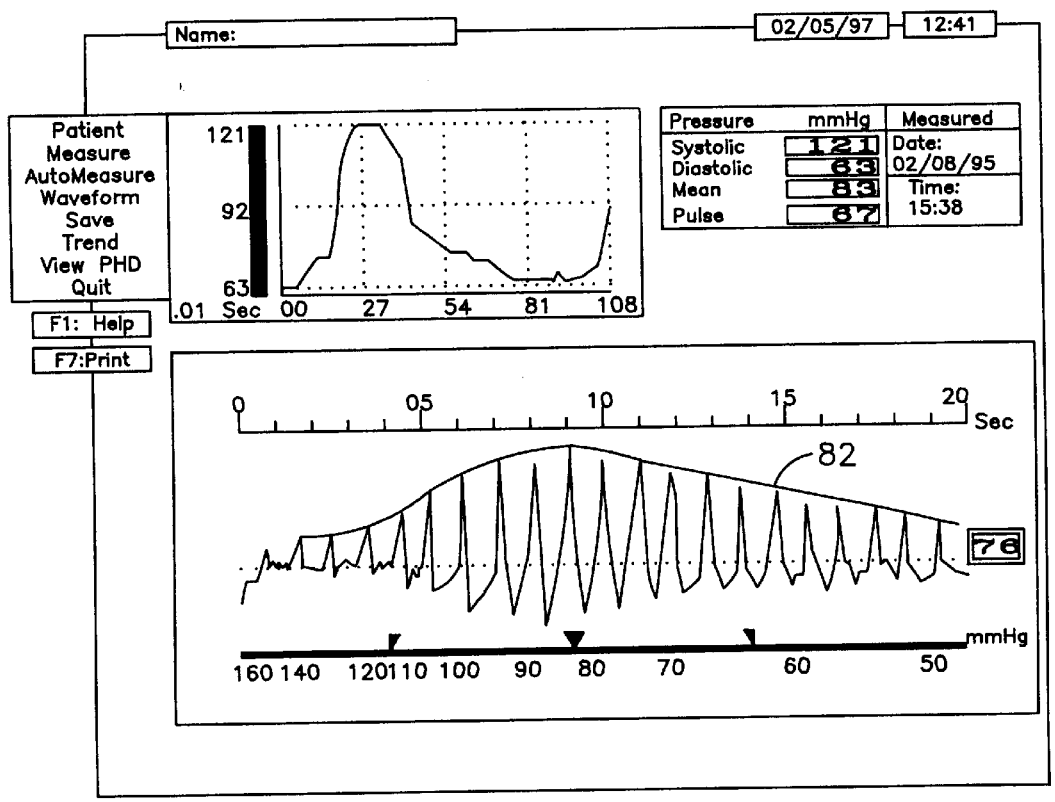

Your attention is now directed to FIGS. 1*a* and 1*b*, which comprise data taken from two patients (here known as patient 1*a* and 1*b*) who have generally normal aortic valves, and do not experience any abnormal aortic regurgitation. The data shown in FIG. 1*a* is data that has been processed by the data processing means to create the array of time dependant pulse wave form data shown in FIGS. 1*a* and 1*b*. It will be noted that the pulse signals occurred over approximately a 27 second time period during which the pressure inducing means varied the pressure induced on the patient, from a high of about 130 mmHg at time 00, to less than 40 mmHg, at time 27 seconds. It will be noted that the data comprises a series of pulsation peaks such as peak 60, and nadir points, such as nadir point 61. In the example shown in FIG. 1*a*, the particular patient had a systolic pressure of 106 mmHg, as indicated by arrow 62, a diastolic pressure of 43 mmHg, as indicated by arrow 64, and mean arterial pressure of 62 mmHg, as indicated by arrow 66.

Your attention is now directed to the peak points of the various wave forms. In this regard, it will be noted that an envelope line 70 is drawn between the adjacent peaks of the pulse wave forms. The overall configuration of the envelope line 70 is generally bell-shaped, rising from a low point that begins as supra systolic pressures, to an apex of the bell, at point 74, which is generally close to the mean arterial pressure point 66, and then descending gradually to another relatively lower end point that occurs at subdiastolic pressures. This reflects that the height of the peaks, generally increases as one moves in the area from supra systolic pressures to the mean arterial pressure, and then generally decreases in the area from the mean arterial pressure to subdiastolic pressures. Importantly, it should be noted that the envelope line 70, although not perfectly bell-shaped, cannot be characterized as undulating or wave-like.

Turning now to the individual peaks, if one were to choose four adjacent peaks from four adjacent wave forms, such as, first peak 60, second adjacent peak 76, third adjacent peak 78 and fourth adjacent peak 80, one would note that the height of the first peak 60 is less than the height of the second peak 76, and that the height of the second peak 76 is less than the height of the third peak 78. The height of the fourth peak 80 is approximately equal to the height of the third peak 78, or possibly slightly lower. Importantly, the general trend of the four peaks is one of generally increasing height and is not one of undulation. This is what you would expect as the envelope line 70 does not itself have an undulating slope.

Turning now to FIG. 1b, you will notice that similar results would be obtained if the peak heights were compared from four adjacent peak points of four adjacent pulse wave forms. Further, the slope of the envelope line 82 is generally bell-shaped, and not undulating. As discussed above, FIGS. 1a and 1b represent data obtained from "normal" patients who did not suffer from any substantial aortic regurgitation.

Figure 2A:
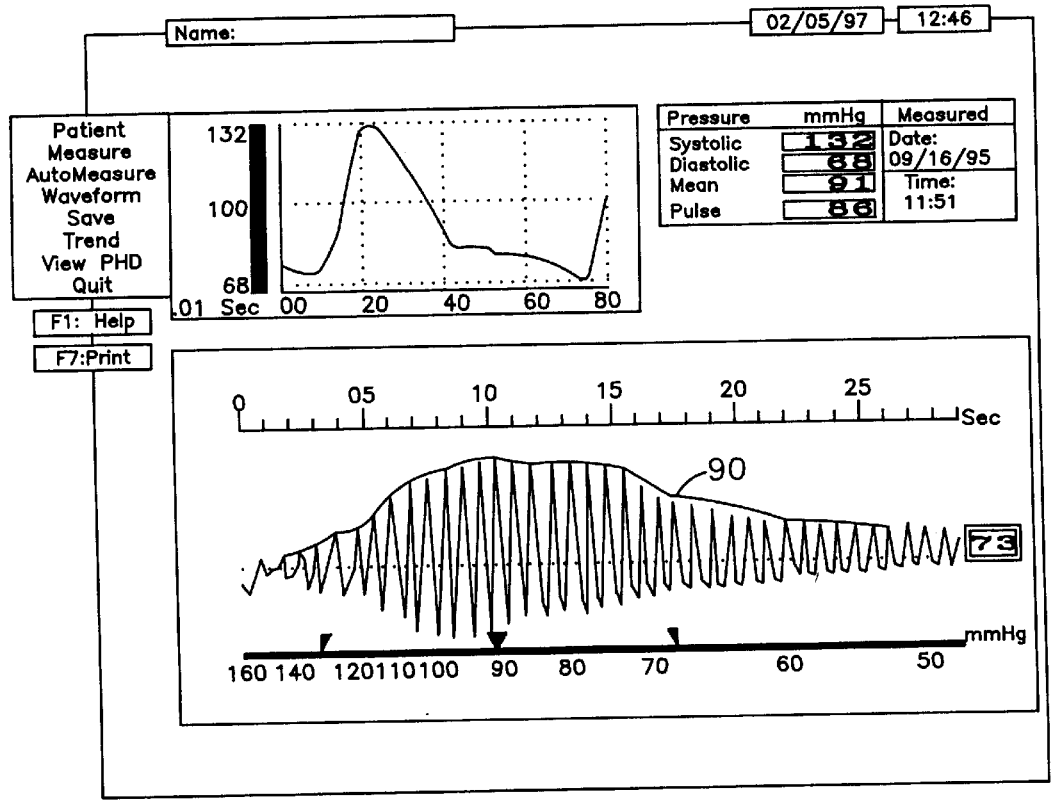
FIGS. 2a and 2b represent displays of pulsation signal data taken from two mild, level-1, aortic regurgitation patients.
Figure 2B:
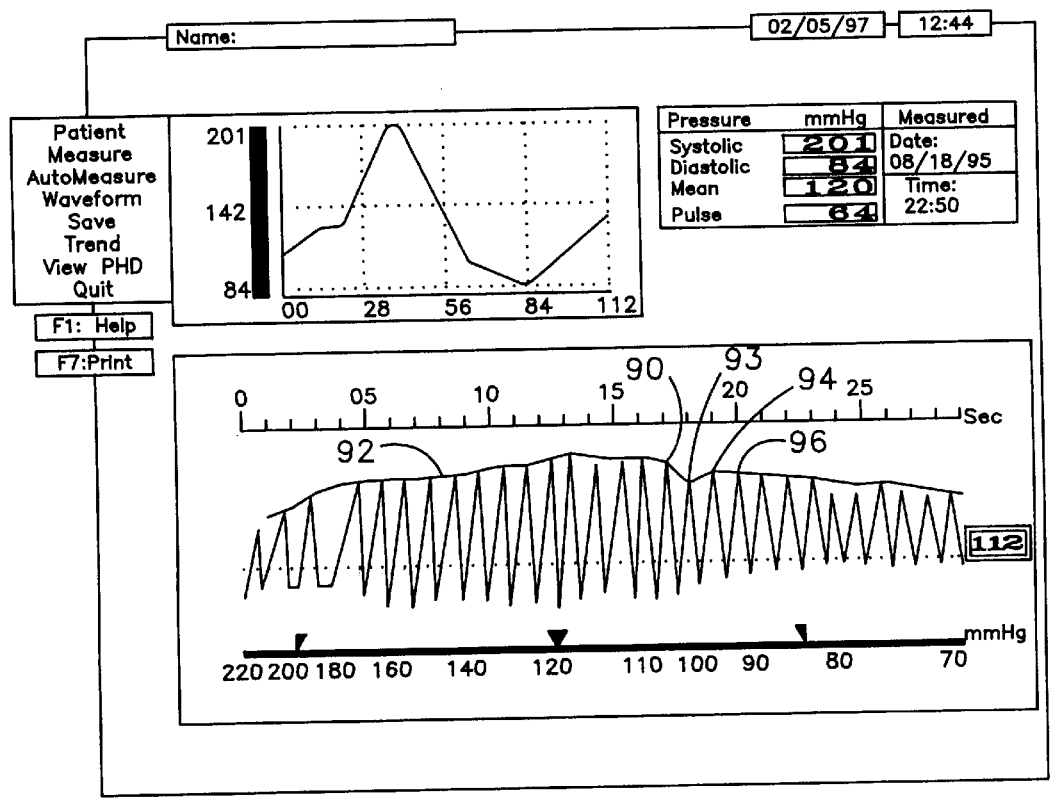

Turning now to FIGS. 2a and 2b, data is shown from patients who have mild aortic regurgitation. It will be noted that the envelope lines 90, 92 and the heights of adjacent peaks do not present as clean of a "bell-shaped" configuration as do the envelope lines 70, 82 of the normal patients of FIGS. 1a and 1b respectively. Turning now to the peak heights, which form the basis for the creation of the envelope lines 90, 92, it will be noted that the heights of adjacent peaks tend to be more varied with regard to whether they are higher or lower than the peaks adjacent to them. For example, turning now to FIG. 2b, it will be noted that the heights of four adjacent peaks 90, 93, 94, 96 are such that the height of peak 90 is greater than the height of peak 93, the height of peak 93 is less than the height of peak 94, and the height of peak 94 is greater than the height of peak 96. Within this small stretch, the slope of the envelope line would be undulating, caused by the sequence of the relatively higher (90), relatively lower (93), relatively higher (94), and relatively lower (96), peak heights of the four adjacent peaks. Nonetheless, it will be noted that the undulation shown in the time dependant pulse wave form data of FIGS. 2a and 2b is slight, and may be difficult to detect without careful observation.

Figure 3A:
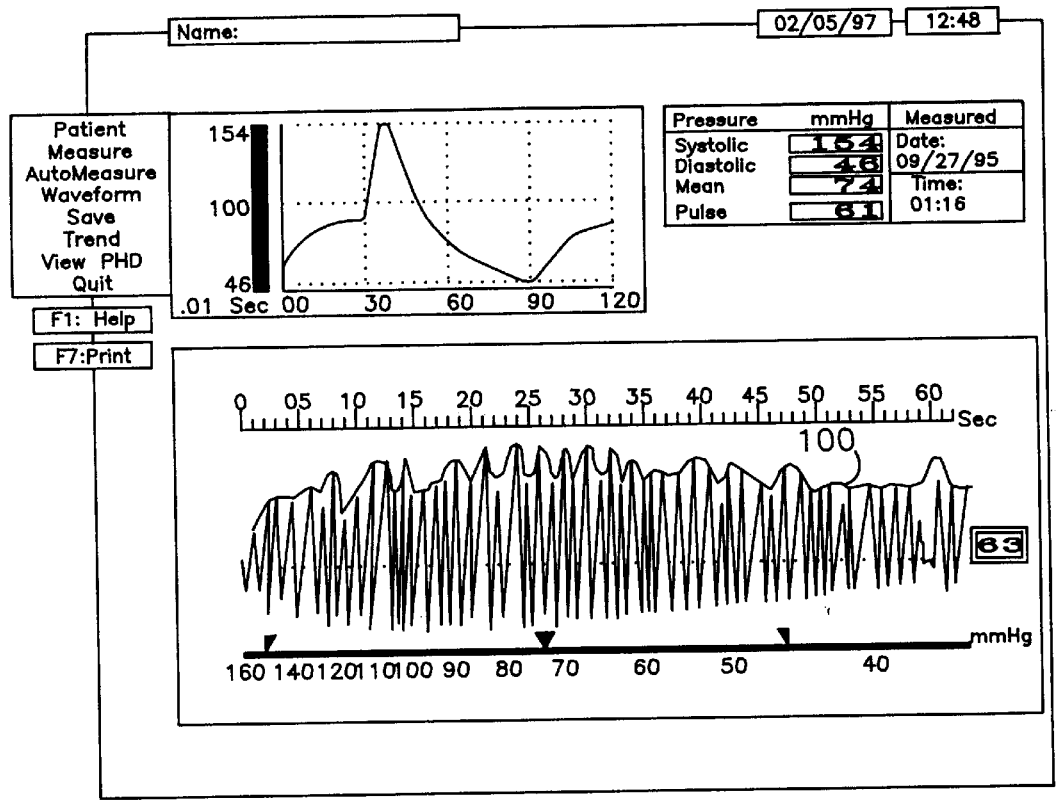
FIGS. 3a and 3b represent displays of pulsation signal data taken from two severe, level-3, aortic regurgitation patients.
Figure 3B:
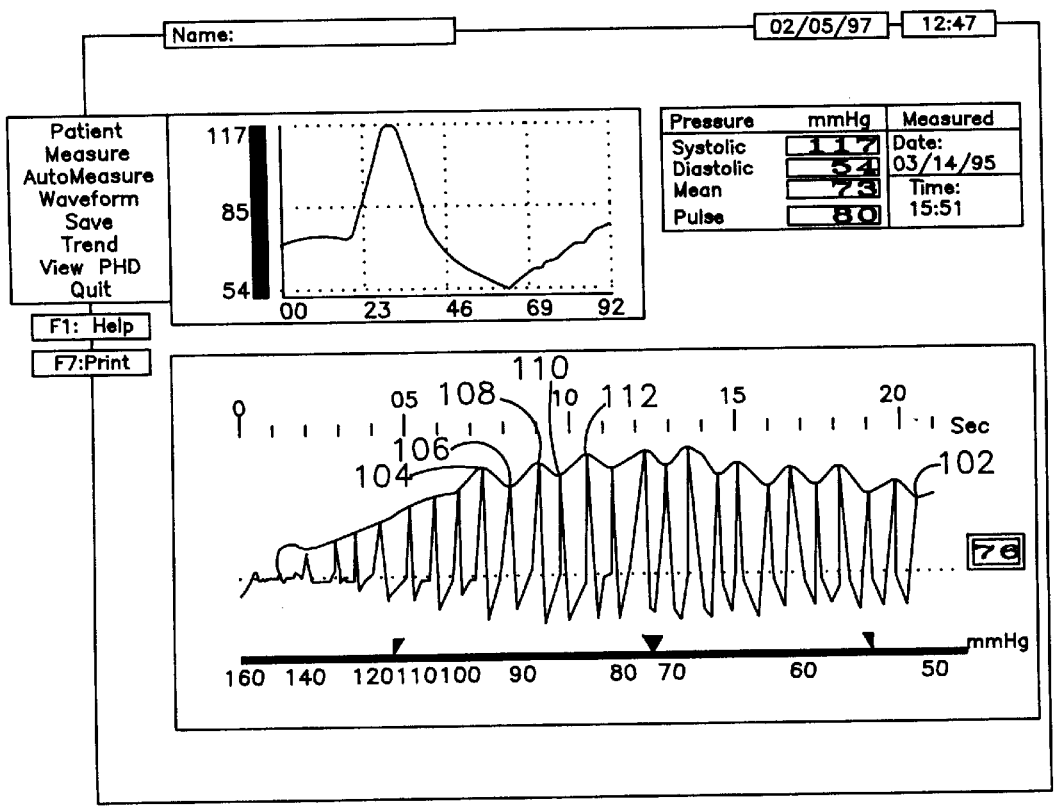

Your attention is now directed to FIGS. 3a and 3b, which show a pair of patients (here known as patients 3a and 3b) who suffer from severe aortic regurgitation. First, it will be noted that the envelope lines 100, 102 which are drawn between adjacent peaks of the time dependant pulse wave form data shown in FIGS. 3a and 3b, each have an undulating slope. This undulating nature is best shown in FIG. 3b with reference to five adjacent peaks, including first adjacent peak 104, second adjacent peak 106, third adjacent peak 108, fourth adjacent peak 110, and fifth adjacent peak 112, having heights $H_1$, $H_2$, $H_3$, $H_4$ and $H_5$ respectively. It will be noted that with these peaks, the following is true: $H_1$ (104)>$H_2$ (106); $H_2$ (106)<$H_3$ (108), $H_3$ (108)>$H_4$ (110) and $H_4$ (110)<$H_5$ (112). This pattern gives rise to the undulating slope of envelope line 102. Because of the severity of the aortic regurgitation of the patients whose data is shown in FIGS. 3a and 3b, the undulations within the envelope line 102, 100 are easily visible to even the uninitiated and can be easily diagnosed as such. The patients whose data is shown in FIG. 3a and 3b were determined by an echo-cardiograph to have level 3 (severe) aortic regurgitation. To the contrary, the patients whose data is shown in FIGS. 2a and 2b were determined by echo-cardiograph to have level one (mild) aortic regurgitation.

As may be apparent from the discussion above, and review of FIGS. 2a and 2b, the use of time dependant pulse wave form data enables the user to easily diagnose the existence of severe aortic regurgitation in patients. However, the diagnosis is more difficult for patients having a more mild degree of aortic regurgitation.

Therefore, it would be helpful if the patient data could be processed in a manner that leads more easily to the identification of those characteristics which suggest the presence of aortic regurgitation. These characteristics can be more easily displayed if the data is processed to convert the time dependant wave form data to an array of frequency dependant wave form data. This conversion is best accomplished by using a Fourier transformation. The data processing means 36 of the present invention can be used in conjunction with the fast Fourier transform program set forth above to convert the time dependant pulsation signal shown in FIGS. 1a–3b to the frequency dependant data shown in FIGS. 4a–6b.

Figure 4A:
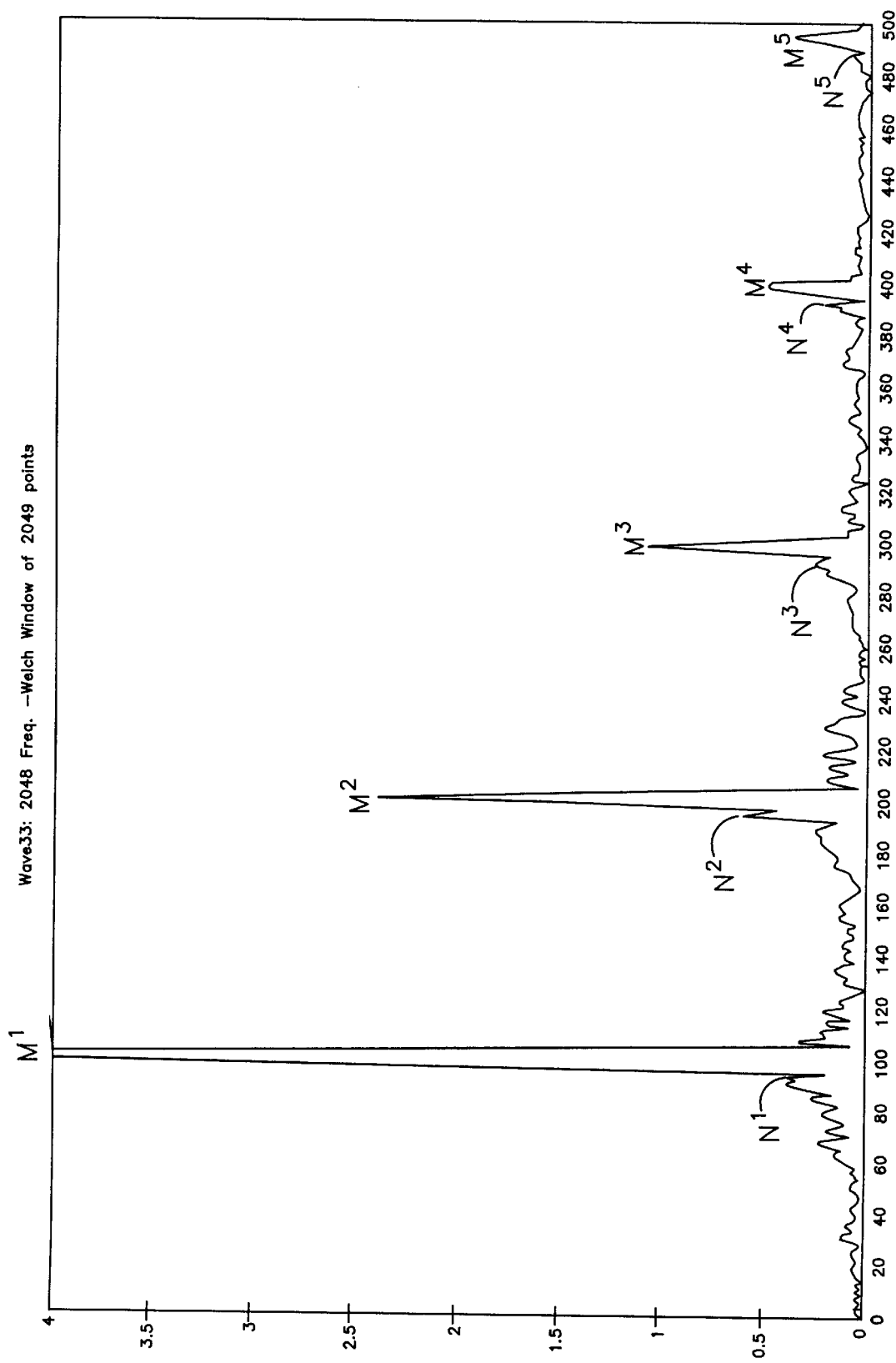
FIGS. 4a and 4b represent displays of frequency dependant, Fourier transformed (FFT) power spectra data of the two normal patients, whose time dependant data is shown in FIGS. 1a and 1b respectively.
Figure 4B:
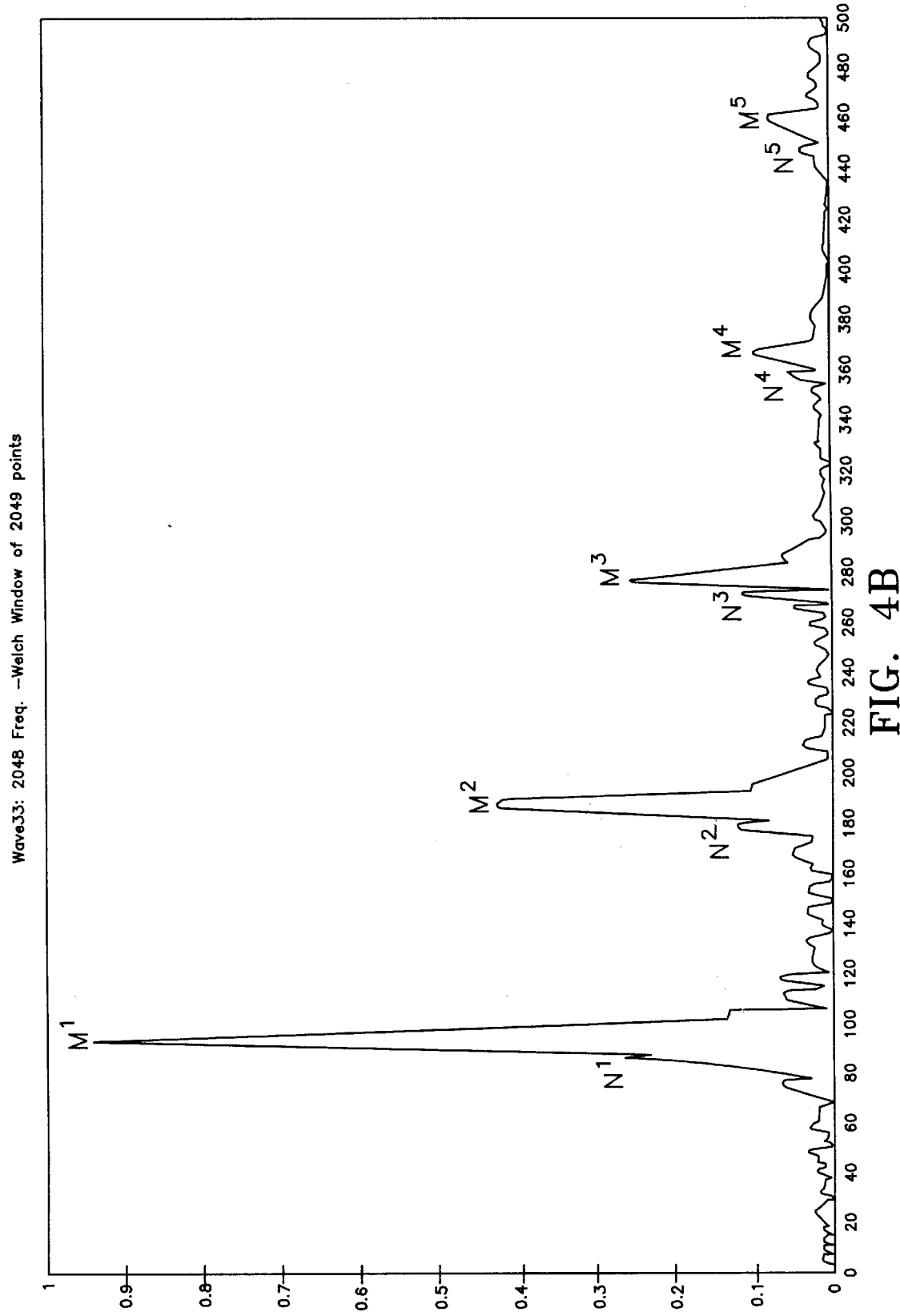

Turning now to FIGS. 4a and 4b, it will be noted that a first series of signals designated as $M^1$, $M^2$, $M^3$, $M^4$ and $M^5$ exist. These signals $M^1$–$M^5$ are the "main" signals, which are representative of the forward flow of fluid out of the ventricle, and through the aortic valve into the aorta. These signals are frequency dependant, and plot the amplitude of the signal, as a function of the frequency.

It will be noted that the "main" frequency signals appear on a graph at frequencies of approximately 100, 200, 300, 400, and 500 Hertz. It will also be noted that a second series of associated peaks designated as $N^1$, $N^2$, $N^3$, $N^4$ and $N^5$ exist. These associated peaks, are lower than the main peaks ($M^1$–$M^5$) but are generally closely associated with the main peaks. Importantly, these second series of peaks ($N^1$–$N^5$) appear at frequencies of approximately 90, 190, 290, 390, and 490 Hz. Since the frequencies of these peaks are not at integral multiples of a fundamental frequency, they are not harmonic, and are treated as noise. If the signals were harmonic, and the first noise signal $N^1$ appeared at a fundamental frequency of 90 Hz, then the second noise signal $N^2$ would have appeared at twice the fundamental frequency $F(N^2)=F(N^1)\times 2$, approximately 180 Hz. Similarly, $N^3$ would have appeared at three times the fundamental frequency, $F(N_3)=F(N^1)\times 3$, approximately 270 Hz; $N^4$ would have appeared four times the fundamental frequency, $F(N_4)=F(N^1)\times 4$, approximately 360 Hz; and $N^5$ would have appeared at five times the fundamental frequency, $F(N_5)=F(N^1)\times 5$, approximately 450 Hz. However, this is not the case. Because these noise signals are not harmonics, these noise signals do not indicate the existence of aortic regurgitation. As such, the absence of any harmonic signals would tend to indicate the absence of any aortic regurgitation.

Although the noise signals $N^1$–$N^5$ of FIG. 4b have a different shape, noise signals $N^1$–$N^5$ are also not harmonic signals. In this regard, it should be noted that main signals $M^1$–$M^5$ of FIG. 4b appear at integral multiples of a fundamental frequency of approximately 92 Hz. Thus, $M^1$ appears at approximately 92 Hz, signal $M^2$ appears at approximately 184 Hz, signal $M^3$ appears at approximately 276 Hz, signal $M^4$ appears at approximately 368 Hz, and signal $M^5$ appears at approximately 460 Hz. Thus, a harmonic distribution is demonstrated with respect to the main signals. This is not the case however with the noise signals of FIG. 4b.

Figure 5A:
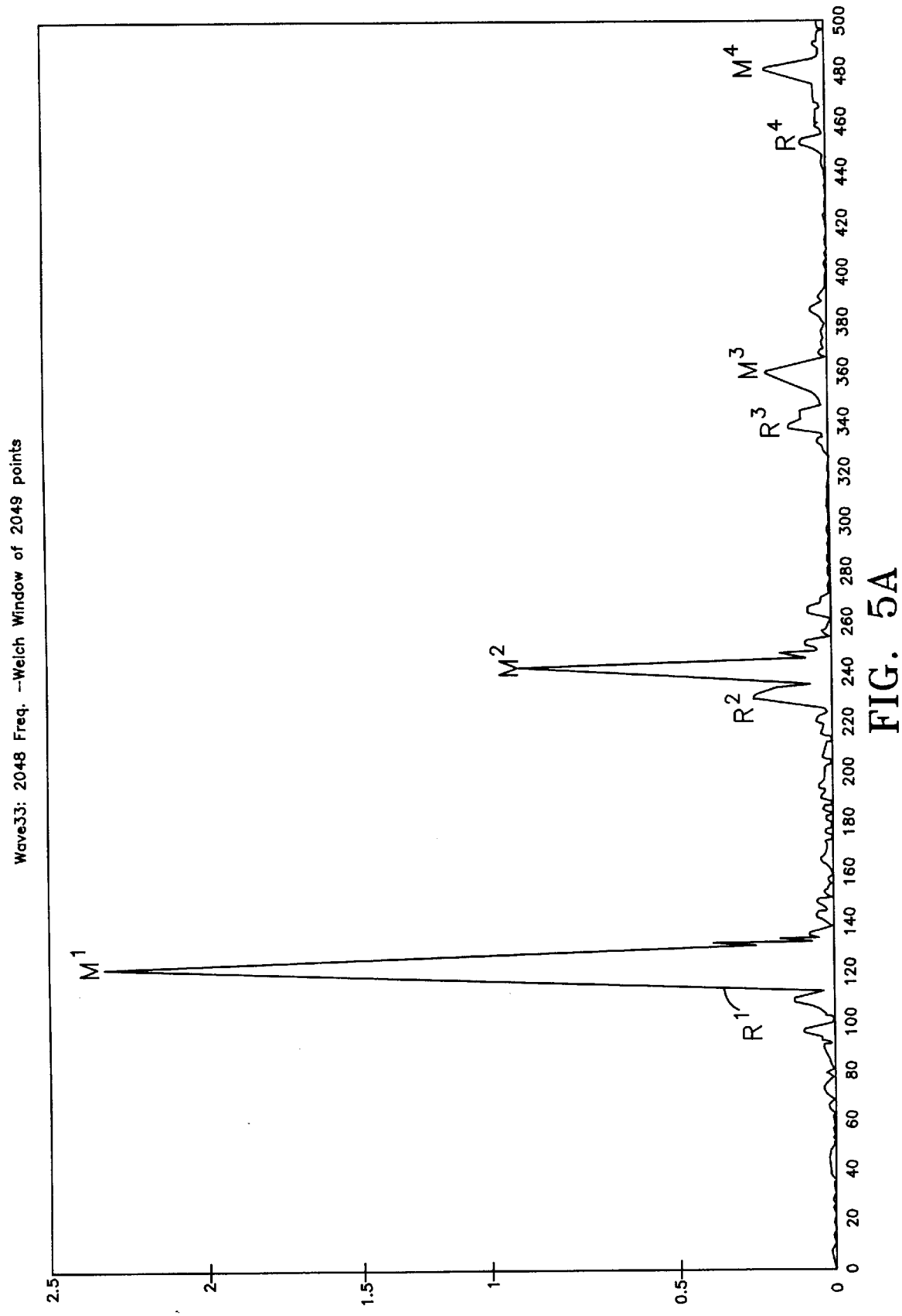
FIGS. 5a and 5b represent displays of frequency dependant, Fourier transformed (FFT) power spectra data of the two mild AR patients, whose time dependant data is shown in FIGS. 2a and 2b respectively.
Figure 5B:
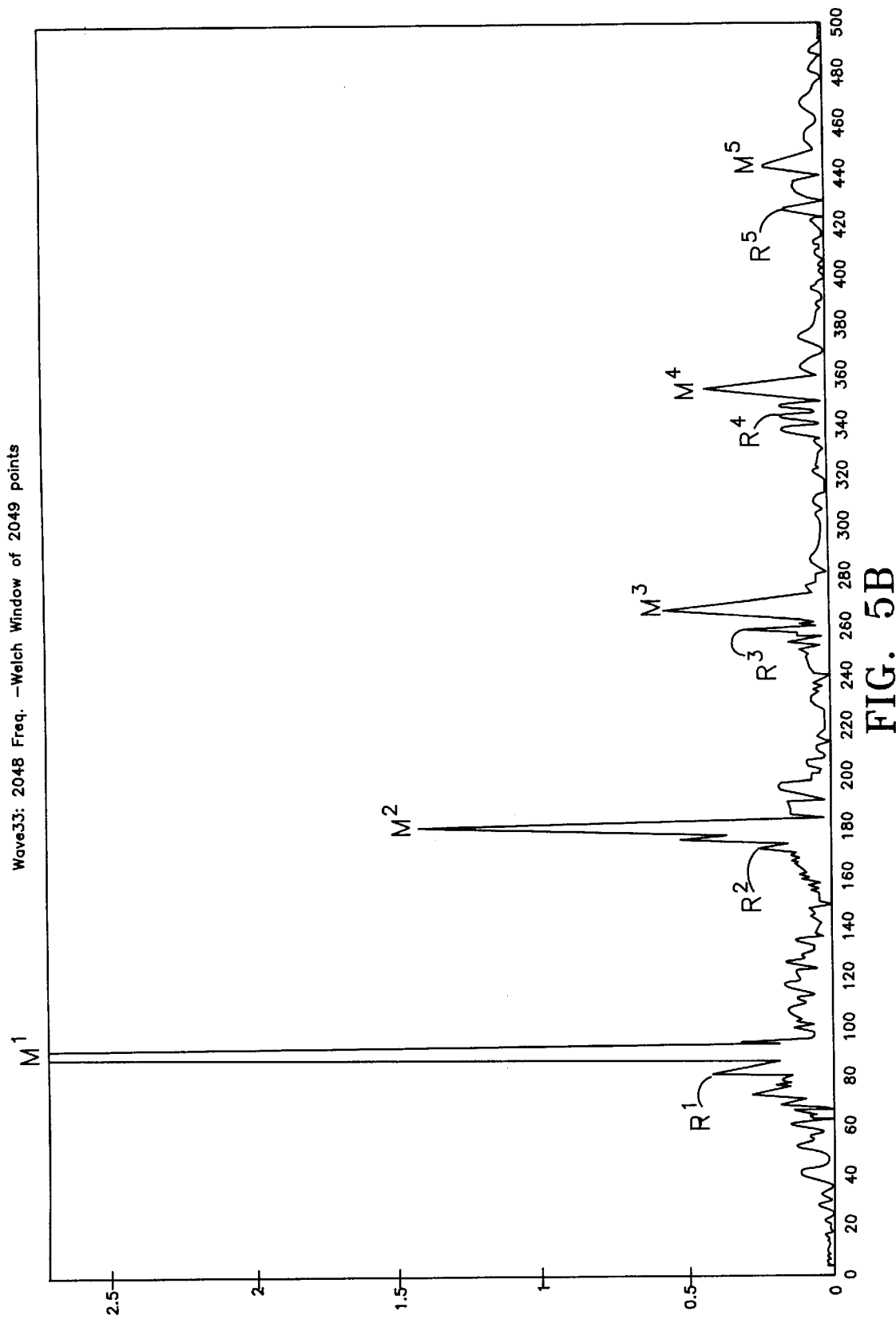

Your attention is now directed to FIGS. 5a and 5b, which correspond generally to the data of the patients shown in FIGS. 2a and 2b respectively. As stated above, the patients of FIGS. 2a and 2b were determined, by echo-cardiograph to have mild aortic regurgitation.

Turning now to FIG. 5a, the main signals $M^1$–$M^4$ appear at integral multiples of the fundamental frequency of 120 Hz. $M^1$ appears at 120 Hz, $M^2$ appears at 240 Hz, $M^3$ appears at 360 Hz and $M^4$ appears at 480 Hz. Similarly, a second series of signal peaks, which reflect aortic regurgitation, are designated by letters $R^1$, $R^2$, $R^3$, and $R^4$.

These regurgitation signals $R^1$–$R^4$ are associated with the respective main peaks $M^1$–$M^4$, respectively, but are harmonically distributed along the frequency axis, at integral multiples of a fundamental frequency of about 114 Hz. In this regard, it should be noted that regurgitation signal $R^1$ is positioned at approximately 114 Hz, $R^2$ at approximately 228 Hz, $R^3$ at approximately 342 Hz and $R^4$ at approximately 456 Hz.

Turning now to FIG. 5b, it will be noted that the second series of signals, $R^1$–$R^5$ are harmonic. In the example shown in FIG. 5b, the peaks of the main signals occur at integral multiples of the fundamental frequency of 89 Hz, thus occurring at approximately 89 Hz ($M^1$), 178 Hz ($M^2$), 267 Hz ($M^3$), 356 Hz ($M^4$), and 445 Hz ($M^5$). Similarly, peaks of the second series of signals $R^1$–$R^5$ occur at multiples of the fundamental frequency of 86 Hz, thus appearing at approximately 86 Hz ($R^1$), 172 Hz ($R^2$), 258 Hz ($R^3$), 344 Hz ($R^4$) and 430 Hz ($R^5$).

In FIGS. 5a and 5b, the existence of the second series of harmonically occurring regurgitation signals $R^1$–$R^5$ indicates the existence of some level of aortic regurgitation within the patients of FIGS. 5a and 5b. Because of the frequency-dependant manner in which the data is displayed, these characteristics indicative of the aortic regurgitation can be determined more easily for patients having low levels of aortic regurgitation, such as the level-1 aortic regurgitation patients for whom the data of FIGS. 5a and 5b was taken.

Figure 6A:
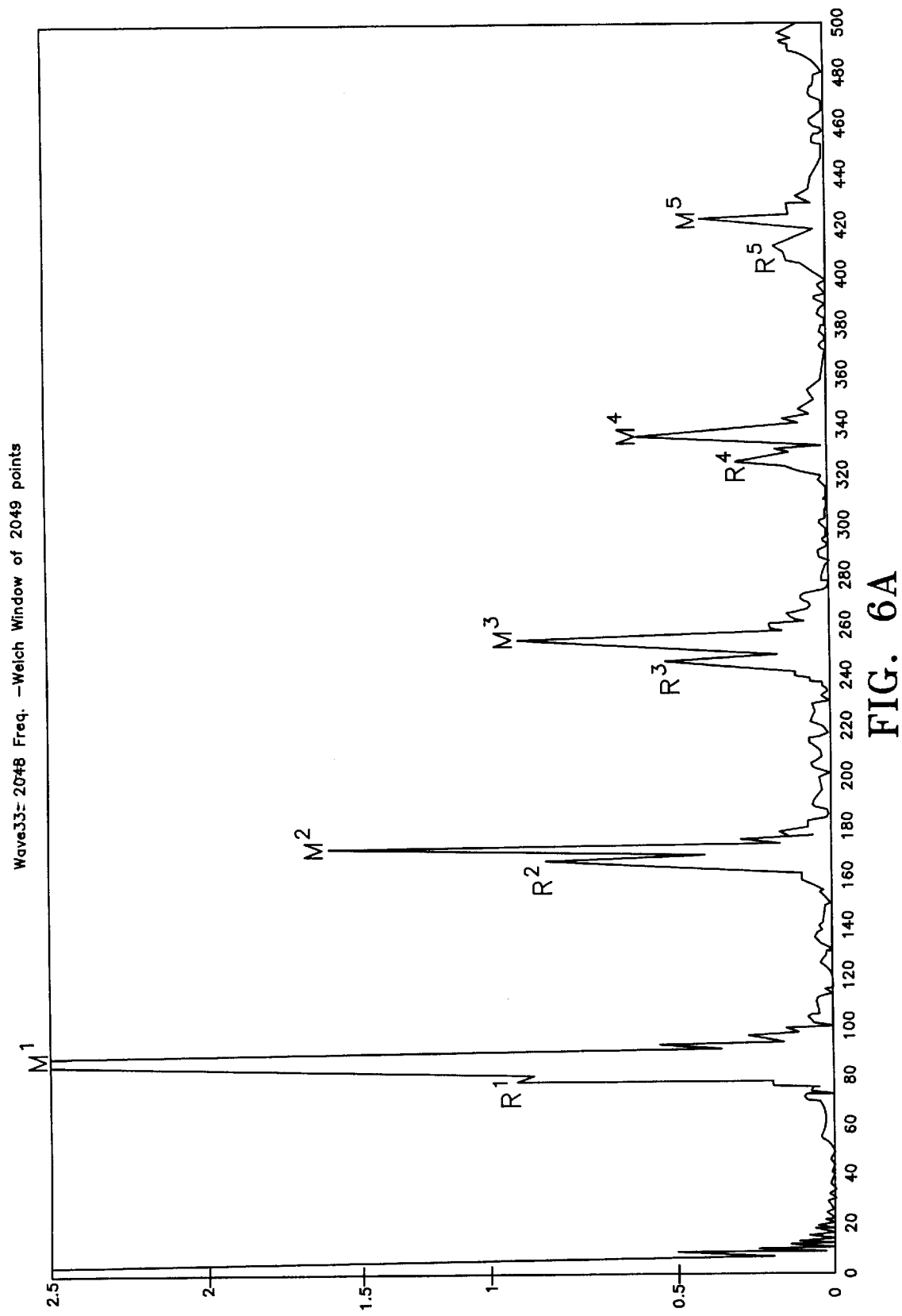
FIGS. 6a and 6b represent displays of frequency dependant, Fourier transformed (FFT) power spectra data of the two severe AR patients, whose time dependant data is shown in FIGS. 3a and 3b respectively.
Figure 6B:
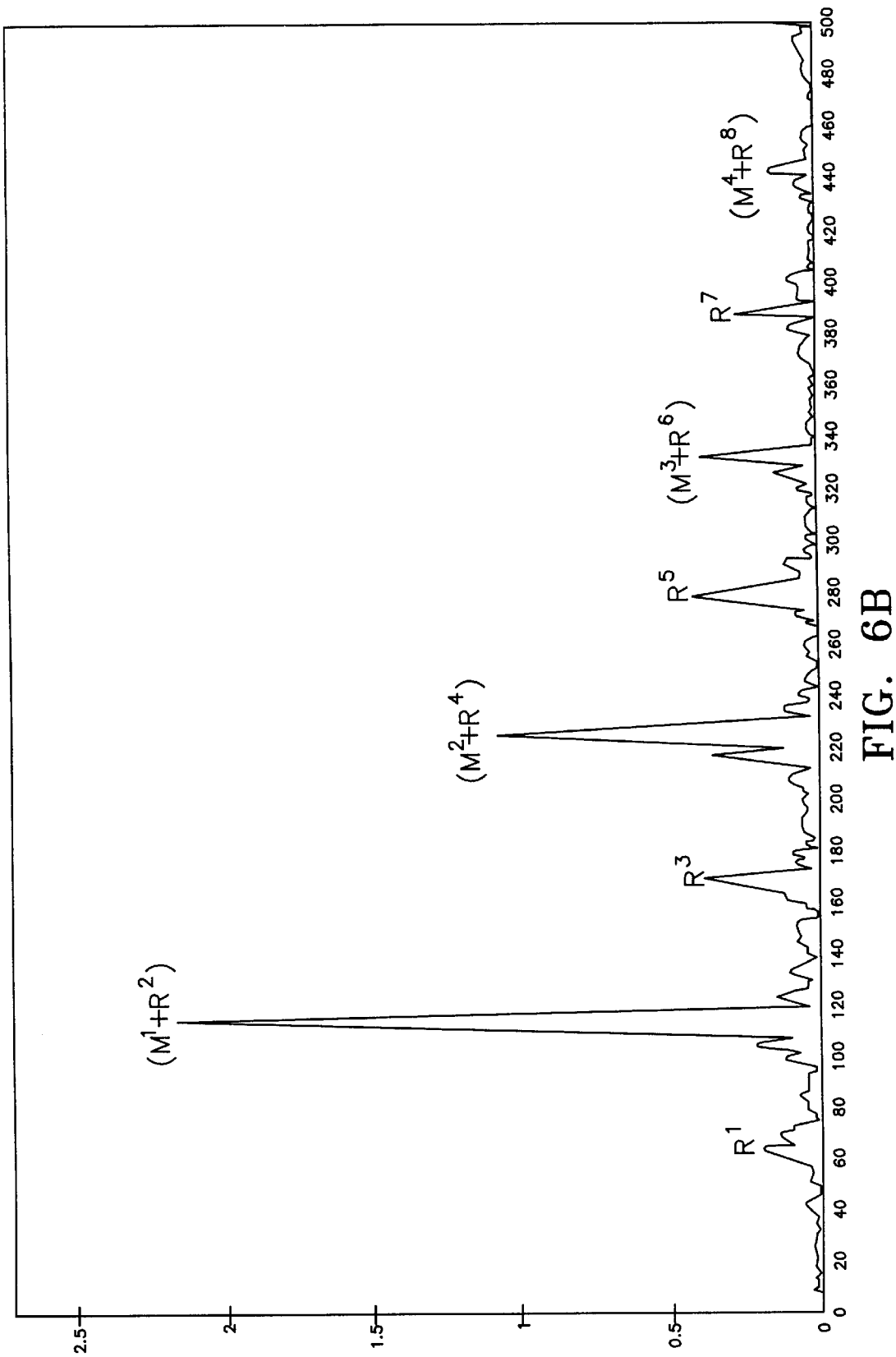

Your attention is now directed to FIGS. 6a and 6b, which show frequency dependant data from patients whose time dependant array of data is shown in FIGS. 3a and 3b. It will be recalled that the patients of FIGS. 3a and 3b were characterized as having severe aortic regurgitation by an echocardiograph test. Turning now to FIG. 6a, it will be noted that there is shown a series of main signals $M^1$–$M^5$, which reflect the flow of fluid forwardly through the aortic valve, and a series of harmonic regurgitation signals $R^1$–$R^5$ which are reflective of aortic regurgitation. Unlike signals $N^1$–$N^5$ of FIGS. 4a and 4b, signals $R^1$–$R^5$ are harmonic signals, occurring at integral multiples of a fundamental frequency of about 82 Hz.

Your attention is now directed to FIG. 6b. FIG. 6b shows a series of four main peaks $M^1$, $M^2$, $M^3$, and $M^4$, and eight regurgitation peaks ($R^1$–$R^8$) which are indicative of aortic regurgitation. It will be noted that the fundamental frequency of the main signal is an integral multiple of the fundamental frequency of the regurgitation signal, thus causing the peaks of the two signals to overlap. For example, the first peak $M^1$ appears at approximately 118 Hz, whereas the corresponding regurgitation signal $R^1$ appears at approximately 59 Hz and the second peak appears at 118 Hz, overlapping with $M^1$. As such, over a given frequency range of 0–500 Hz, as shown in the drawing, twice as many regurgitation signals exist as main flow signals, due to the fact that the fundamental frequency of the regurgitation signal is one-half the fundamental frequency of the main signal.

It has been found by the applicants that much useful information can be derived about the nature of the aortic regurgitation, and in particular, about the relative volume of aortic regurgitant flow by comparing the signals representative of the main flow forwardly through the aortic valve (e.g. $M^1$–$M^5$), to the signals representative of the regurgitant flow of fluid, represented by the regurgitation signals (e.g. $R^1$–$R^5$).

Turning now to each of FIGS. 5a–6b, it will be noted that each of the main flow signals have an amplitude $A_1$ which corresponds to the height of the peaks. Similarly, the regurgitation flow signals $R^1$–$R^5$ also have an amplitude $A_2$. By comparing the amplitude of the regurgitation flow signals to the amplitude of the main signals, one can obtain some semi-quantitative analysis of the relative volume of the regurgitation flow, to the main flow. This semi-quantitative analysis can be performed through the equation $A_2 \div A_1$, wherein $A_2$ equals the amplitude of the regurgitation flow signals ($R^1$–$R^5$), and $A_1$ equals the amplitude of the main flow signals ($M^1$–$M^5$). This can be done by using one main signal (e.g. $M^3$), and one corresponding regurgitation signal (i.e. $R^3$), or by using several signals.

Turning now to Table 1, this analysis was performed wherein the Amplitude $A_2$ of the second harmonic $R^2$ was divided by the amplitude $A_1$, of the second harmonic of the main signal $M^2$. However, for FIG. 6b, because of the overlap, $R^2$ was approximated as $(R^1+R^3)/2$. For the main signal, $M^2$ was derived by a calculation which sought to subtract the $R^4$ contribution at the second harmonic of the main signal $M^2$. Thus the equation $(M^2+R^4)-(R^3+R^5)/2=M^2$ was used, as shown in Table 1.

TABLE 1

DYNAPULSE WAVEFORM FFT FREQUENCY ANALYSIS:
Identify aortic "Regurgitation", A.R., wave spectrum (R) &
Estimate its weight (in %) vs. "Main" pulse wave spectrum (M).

| CASE-# | Frequency (Hz) | | i = 1 | i = 2 | i = 3 | i = 4 | i = 5 | R2/M2 (×100%) | NOTES |
|---|---|---|---|---|---|---|---|---|---|
| AR CASES: | f(M1) | f(R1) | [f(Mi) – f(Ri)] (Hz) | | | | | | |
| SEVERE-1 | 1.04 | 1.00 | 0.03 | 0.07 | 0.10 | 0.13 | 0.16 | 55% | |
| SEVERE-2 | 1.36 | 0.68 | 0.67 | 1.34 | 2.00 | 2.67 | | 44% | * |
| MILD-1 | 1.46 | 1.38 | 0.07 | 0.15 | 0.20 | 0.27 | | 26% | |
| MILD-2 | 1.09 | 1.05 | 0.04 | 0.08 | 0.12 | 0.15 | 0.22 | 20% | |
| NORMAL CASES: | f(M1) | f(N1) | [f(Mi) – f(Ni)] (Hz): | | | | | | N = Noise |
| NORMAL-1 | 1.21 | 1.13 | 0.08 | 0.08 | 0.08 | 0.08 | 0.08 | 0% | ** |
| NORMAL-2 | 1.12 | 1.04 | 0.08 | 0.08 | 0.08 | 0.08 | 0.08 | 0% | |

*Due to overlap of R and M spectra, R2 and M2 were calculated by following equation:
R2 = (R1 + R3)/2
M2 = (M2 + R4) – (R3 + R5)/2; ASSUMING R4 = (R3 + R5)/2
***"Noise" FFT signals (N) associate to the "Main" spectrum signals at a fixed distance in frequency domain, ie. [f(Mi) – f(Ni)] = constant. Where, "Regurgitation" FFT spectrum signal had the [f(Mi) – f(Ri)] value that increased from i = 1 to i = 5 and as a multiple of i.

Turning now to the second-to-the-last column of Table 1, it will be noted that the approximated percentage of regurgitation volume to main volume was 55% and 44% for the respective patients whose data is shown in FIGS. 6a and 6b respectively. As set forth in more detail above, these patients were both diagnosed to have severe aortic regurgitation.

For the patients whose data is shown in FIGS. 5a and 5b, who were diagnosed with a more mild aortic regurgitation, the regurgitation volumes were calculated to be 26%, for the patient of FIG. 5a, and 20%, for the patient of FIG. 5b.

As the patients whose data is shown in FIGS. 4a and 4b had no regurgitation, as their signal display lacked any harmonic regurgitation signal, these patients were diagnosed as having a "0" percent regurgitation flow.

To achieve the calculations shown in Table 1, the various amplitudes of the signals were measured and compared. However, it is also possible, and may be advisable to compare the "density" of the two signals to each other, as such a density measurement would also tend to lead to a semi-quantitative analysis of the regurgitation flow relative to the forward flow. Such a comparison of density could be done by determining the area under the respective signals (e.g. $M^1$, $R^1$), and comparing them in a manner similar, such as by dividing the area under the regurgitant flow signal ($D_2$) by the area under the main signal ($D_1$), by the equation regurgitant relative volume percentage equals $D_2 \div D_1$.

Additionally, other computer modeling methods may be used to help determine relative flow volume.

It is also believed that the frequency shift between the position of the main signal (e.g. $M^1$) and its correspondent regurgitation signal ($R^1$) will provide valuable data about the nature, type and characteristics of the aortic regurgitation of the patient.

What is claimed is:

1. A method for identifying the existence of aortic valve abnormalities in a patient comprising the steps of:
   (1) providing a non-invasive pressure inducing means for inducing a pressure on a body part of a patient and applying pressure to the body part;
   (2) providing a data receiving means;
   (3) using the data receiving means to receive a stream of pulsation signal data from the patient relating to the pressure response of pulsed fluid flowing through the cardiovascular system of the patient;
   (4) providing a data processing means;
   (5) using the data processing means for processing the stream of pulsation signal data to create an array of pulse wave forms; and
   (6) identifying wave form characteristics that denote the presence of aortic valve abnormalities.

2. The method of claim 1 wherein the step of using the data processing means comprises the step of using the data processing means to create a time dependant array of pulse wave forms.

3. The method of claim 2 wherein each of the pulse wave forms of the time dependant array of pulse wave forms includes a peak, and the step of identifying wave form characteristics includes the step of comparing the height of a series of adjacent wave form peaks.

4. The method of claim 3 wherein the step of comparing the height of a series of adjacent wave form peaks includes the step of comparing the height of at least four adjacent peaks, $P_1$, $P_2$, $P_3$ and $P_4$, having heights of $H_1$, $H_2$, $H_3$ and $H_4$, respectively.

5. The method of claim 4 further comprising the step of detecting the presence of aortic valve abnormalities if at least one of (1): $H_1 > H_2$, $H_2 < H_3$, and $H_3 > H_4$; and (2): $H_1 < H_2$, $H_2 > H_3$ and $H_3 < H_4$ occurs.

6. The method of claim 1 wherein the array of pulse wave forms comprises a series of at least four adjacent pulse wave forms including a first wave form having a peak $P_1$, and a height $H_1$; a second pulse wave form having a peak $P_2$ and a height $H_2$; a third pulse wave form having a peak $P_3$ and a height $H_3$; and a fourth pulse wave form having a peak $P_4$ and a height $H_4$; further comprising the step of detecting the presence of aortic valve abnormalities if at least one of: (1) $H_1 > H_2$, $H_2 < H_3$, and $H_3 > H_4$; and (2) $H_1 < H_2$, $H_2 > H_3$ and $H_3 < H_4$ occurs.

7. The method of claim 1 further comprising the step of graphically displaying the array of pulse wave forms.

8. The method of claim 7 wherein
   (1) the step of using the data processing means comprises the step of using the data processing means to create a time dependant array of pulse wave forms,
   (2) the time dependant array of pulse wave forms are graphically displayed,
   (3) the time dependant array of pulse wave forms being graphically displayed include a series of pulse wave forms each having a peak,
   (4) the step of graphically displaying the time dependant array includes the step of displaying an envelope line that extends between the peaks of adjacent wave forms, and
   (5) the step of identifying wave form characteristics includes the step of identifying the slope of the envelope line to determine whether it denotes the presence of aortic valve abnormalities.

9. A method for identifying the existence of aortic valve abnormalities, comprising the steps of:
   (1) providing a non-invasive pressure inducing means for inducing a pressure on a body part of a patient and applying pressure to the body part;
   (2) providing a data receiving means;
   (3) using the data receiving means to receive a stream of pulsation signal data from the patient relating to the pressure response of pulsed fluid flowing through the cardiovascular system of the patient having a cardiovascular system;
   (4) providing a data processing means;
   (5) processing the stream of pulsation signal data to create an array of time dependant wave form data;
   (6) converting the array of time dependant wave form data to an array of frequency dependant wave form data; and
   (7) identifying characteristics of the frequency dependant wave form data that denote the presence of aortic valve abnormalities.

10. The method of claim 9 wherein the steps of converting the time dependant wave form data comprises the step of using a Fourier transformation to convert the time dependant wave form data to frequency dependant wave form data.

11. The method of claim 9 wherein the step of identifying the characteristics of the frequency dependant wave form data includes the step of identifying a first series of harmonically occurring flow signals corresponding to a flow of fluid forwardly through the aortic valve, and detecting the presence or absence of a second series of harmonically occurring flow signals corresponding to aortic regurgitation.

12. The method of claim 11 wherein the flow signals of the first series each have a corresponding flow signal of the second series, each of the flow signals of the first series has an amplitude $A_1$, and each of the flow signals of the second series has an amplitude $A_2$ and further comprising the step of comparing the amplitude $A_2$ of a flow signal of the second series to the amplitude $A_1$ of a flow signal of the first series to obtain a semi-quantitative analysis of the aortic regurgitation.

13. The method of claim 12 wherein the step of comparing the amplitudes comprises the step of determining a ratio $A_2/A_1$ of the amplitudes of corresponding flow signals of the second and first series to approximate the ratio of aortic regurgitation flow to forward fluid flow through the aortic valve.

14. The method of claim 11 wherein the flow signals of the first series each have a corresponding flow signal of the second series, each of the flow signals of the first series has a density, $D_1$
each of the flow signals of the second series has a density, $D_2$ and
further comprising the step of comparing the density $D_2$ of the flow signal of the second series to the density $D_1$ of the flow signal of the first series to obtain a semi-quantitative value of the aortic regurgitation.

15. The method of claim 14 wherein the step of comparing the densities comprises the step of determining the ratio $D_2/D_1$ of corresponding flow signals of the second and first series to approximate the ratio of aortic regurgitation flow, to the flow of fluid forward through the aortic valve.

16. The method of claim 11 further comprising the step of evaluating the frequency shift between the flow signals of the first series and the flow signals of the second series.

17. The method of claim 16 wherein the step of evaluating the frequency shift comprises the step of evaluating the frequency shift between the flow signals of the first series and the flow signals of the second series to determine at least one of the nature, type and characteristics of the aortic regurgitation of the patient.

18. A device for identifying the existence of aortic valve abnormalities in a patient comprising:
   (1) a non-invasive pressure inducing means for inducing a pressure to a body part of a patient;
   (2) a data receiving means for receiving a stream of pulsation signal data from the patient relating to the pressure response of pulsed fluid flowing through the cardiovascular system of the patient;
   (3) a data processing means for processing the stream of pulsation signal data to create a time dependant array of pulse wave forms; and
   (4) means for aiding in the identification of wave form characteristics that denote the presence of aortic valve abnormalities.

19. The device of claim 18 further comprising graphic display means for displaying the time dependant array of pulse wave forms.

20. The device of claim 18 wherein each of the pulse wave forms of the time dependant array of pulse wave forms includes a peak, and the means for aiding in the identification of wave form characteristics includes means for aiding in the comparison of the height of a series of adjacent wave form peaks.

21. The device of claim 20 wherein the means for aiding in the comparison includes means for aiding in the comparison of the height of at least four adjacent peaks, $P_1$, $P_2$, $P_3$ and $P_4$, having heights of $H_1$, $H_2$, $H_3$ and $H_4$, respectively.

22. The device of claim 21 further comprising means for detecting the presence of aortic valve abnormalities if at least one of: $H_1>H_2$, $H_2<H_3$, and $H_3>H_4$; and $H_1<H_2$, $H_2>H_3$ and $H_3<H_4$ occurs.

23. The device of claim 18 wherein the time dependant array of pulse wave forms comprises a series of at least four adjacent pulse wave forms including a first wave form having a peak $P_1$, and a height $H_1$; a second pulse wave form having a peak $P_2$ and a height $H_2$; a third pulse wave form having a peak $P_3$ and a height $H_3$; and a fourth pulse wave form having a peak $P_4$ and a height $H_4$; further comprising means for detecting the presence of aortic valve abnormalities if at least one of: $H_1>H_2$, $H_2<H_3$, and $H_3>H_4$; and $H_1<H_2$, $H_2>H_3$ and $H_3<H_4$ occurs.

24. The device of claim 18 further comprising means for graphically displaying the time dependant array of pulse wave forms, wherein the time dependant array of pulse wave forms displayed by the graphic display means includes a series of pulse wave forms each having a peak, and the graphic display means includes means for displaying an envelope line that extends between the peaks of adjacent wave forms, and the means for aiding in the identification of wave form characteristics includes means for identifying the slope of the envelope line to determine whether it denotes the presence of aortic valve abnormalities.

25. The device of claim 24 wherein the means for identifying the slope of the envelope line comprises means for determining whether the envelope line has an undulating slope, thereby suggesting the presence of aortic valve abnormalities.

26. A device for identifying the existence of aortic valve abnormalities, comprising:
   (1) a non-invasive pressure inducing means for inducing a pressure to a body part of a patient;
   (2) a data receiving means for receiving a stream of pulsation signal data from the patient relating to the pressure response of pulsed fluid flowing through a cardiovascular system of the patient;
   (3) a data processing means for processing the stream of pulsation signal data to create an array of time dependant wave form data;
   (4) means for converting the array of time dependant wave form data to an array of frequency dependant wave form data; and
   (5) means for aiding in the identification of characteristics of the frequency dependant wave form data that denote the presence of aortic valve abnormalities.

27. The device of claim 26 wherein the means of converting the time dependant wave form data comprises a program means using a Fourier transformation to convert the time dependant wave form data to frequency dependant wave form data.

28. The device of claim 26 wherein the means for aiding in the identification of the characteristics of the frequency dependant wave form data includes means for aiding in the identification of a first series of harmonically occurring flow signals corresponding to a flow of fluid forwardly through the aortic valve, and in the detection of the presence or absence of a second series of harmonically occurring flow signals corresponding to aortic regurgitation.

29. The device of claim 28 wherein the flow signals of the first series each have a corresponding flow signal of the second series, each of the flow signals of the first series has an amplitude $A_1$, and each of the flow signals of the second series has an amplitude $A_2$ and further comprising means for comparing the amplitude $A_2$ of a flow signal of the second series to the amplitude $A_1$ of a flow signal of the first series to obtain a semi-quantitative analysis of the aortic regurgitation.

30. The device of claim 29 wherein the means for comparing the amplitudes comprises means for determining a ratio $A_2/A_1$ of the amplitudes of corresponding flow signals of the second and first series to approximate the ratio of aortic regurgitation flow to forward fluid flow through the aortic valve.

31. The device of claim 28 wherein the flow signals of the first series each have a corresponding flow signal of the second series, each of the flow signals of the first series has a density, $D_1$ each of the flow signals of the second series has a density, $D_2$ and further comprising means for comparing the density $D_2$ of the flow signal of the second series to the density $D_1$ of the flow signal of the first series to obtain a semi-quantitative value of the aortic regurgitation.

32. The device of claim 31 wherein the means for comparing the densities comprises means for determining the ratio $D_2/D_1$ of corresponding flow signals of the second and first series to approximate the ratio of aortic regurgitation flow, to the flow of fluid forward through the aortic valve.

* * * * *